United States Patent [19]

Blair et al.

[11] Patent Number: 4,698,440

[45] Date of Patent: Oct. 6, 1987

[54] PROCESS FOR MAKING N-BUTYL METHACRYLATE

[75] Inventors: Leslie M. Blair, Parkersburg; Roddy M. Conrad, Charleston, both of W. Va.

[73] Assignee: E. I. Du Pont de Nemours and Company, Wilmington, Del.

[21] Appl. No.: 762,207

[22] Filed: Aug. 5, 1985

Related U.S. Application Data

[63] Continuation of Ser. No. 532,040, Sep. 14, 1983.

[51] Int. Cl.[4] .............................................. C07C 67/08
[52] U.S. Cl. .................................. 560/205; 560/218; 203/DIG. 6; 203/DIG. 21
[58] Field of Search ............................. 560/205, 218; 203/DIG. 6, DIG. 21

[56] References Cited

U.S. PATENT DOCUMENTS

| | | | |
|---|---|---|---|
| 3,639,460 | 2/1972 | Wenzel et al. | 260/486 |
| 3,776,947 | 12/1973 | Shimizu et al. | 260/486 |
| 4,076,950 | 2/1978 | Stewart et al. | 560/218 |
| 4,250,328 | 2/1981 | Fujita et al. | 560/205 |
| 4,280,010 | 7/1981 | Erpenbach et al. | 560/205 |

FOREIGN PATENT DOCUMENTS

| | | | |
|---|---|---|---|
| 1288596 | 2/1969 | Fed. Rep. of Germany | 560/205 |
| 1017522 | 1/1966 | United Kingdom | 560/205 |

*Primary Examiner*—Michael L. Shippen
*Assistant Examiner*—Bruce D. Gray

[57] ABSTRACT

A batch process for preparing n-butyl methacrylate directly from n-butanol and methacrylic acid by employing azeotropic distillation and azeotropic phase separation.

1 Claim, 2 Drawing Figures

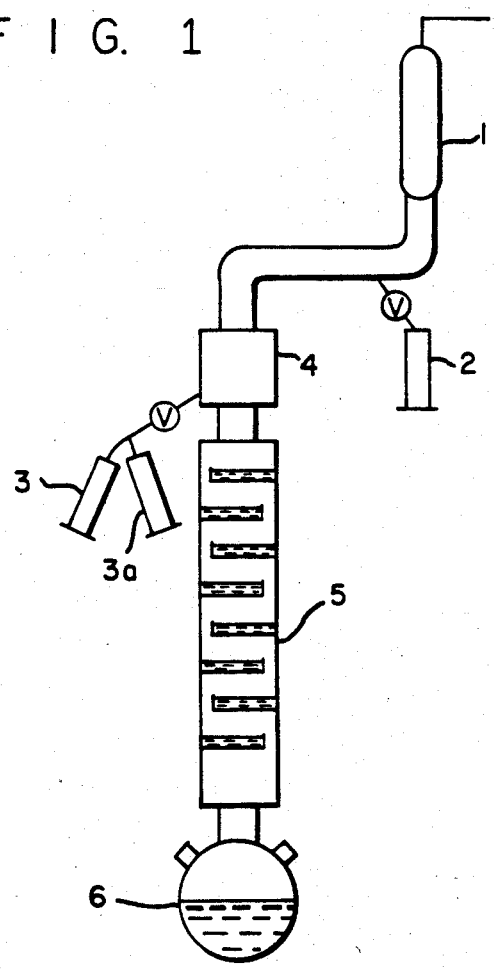
F I G. 1

PROCESS FOR MAKING N-BUTYL METHACRYLATE

This application is a continuation of application Ser. No. 532,040 filed Sept 14, 1983.

BACKGROUND OF THE INVENTION

This invention relates to the preparation of n-butyl methacrylate directly from the esterification of methacrylic acid and n-butyl alcohol.

N-butyl methacrylate is conveniently prepared by a transesterification reaction. However, it would be advantageous to prepare n-butyl methacrylate by direct esterification because it provides a more efficient, higher capacity process, i.e., a higher production rate process. But, it is difficult to separate the product from methacrylic acid reactant because of their similar boiling points. Therefore, it would be desirable to find a practical and economical method of directly esterifying methacrylic acid and n-butanol.

SUMMARY OF THE INVENTION

The process of this invention employs a unique combination of reaction equilibria, azeotropic distillation, and phase separation to manufacture n-butyl methacrylate at an improved production rate over the transesterification process.

Methacrylic acid is reacted with n-butanol in the pot of a batch distillation still. Virtual complete reaction to the butyl ester is achieved by distilling off the water of reaction in the form of an n-butanol-water azeotrope. This shifts the reaction equilibria to the butyl methacrylate product, and reduces methacrylic acid concentration.

In contrast to the transesterification route, the n-butanol-water azeotrope condenses to a water-rich and a water-poor (or, conversely, a butanol-rich) layer. Thus, by equipping the distillate condenser with a decanter, the azeotrope is collected and condensed, and the the water-rich layer is removed. The n-butanol-rich layer is then returned as reflux liquid to the distillation column. This return of n-butanol allows more n-butyl methacrylate to be made per equivalent pot charge than heretofore was possible with the transesterification procedure because this latter procedure results in a one-phase distillation condensate in which the ingredients are difficult to separate.

Thus, a preferred aspect of the process of this invention is a batch process for making n-butyl methacrylate which comprises reacting methacrylic acid and n-butanol in a reaction vessel equipped with a distillation column, said vessel also containing a strong acid catalyst present in an amount of between 0.5 to 6 percent by weight based on total weight of reaction mixture, the initial mole ratio of n-butanol to methacrylic acid being between 1.1 to 1.5, the temperature in the reaction vessel being maintained between 95° and 120° C. and the pressure being between 30 and 150 kPa, while a. collecting gaseous n-butanol-water azeotrope distillate from the distillation still,
b. condensing the azeotrope distillate collected in step a.,
c. separating the water-rich layer from the n-butanol-rich layer of the distillate condensed in step b, and
d. returning the n-butanol-rich layer as reflux liquid to the distillation column, said process being carried out until the methacrylic acid is substantially used up.

DRAWINGS

FIG. 1 depicts one distillation apparatus used herein.
FIG. 2 depicts another distillation apparatus used herein.

DETAILED DESCRIPTION

Figure 2:
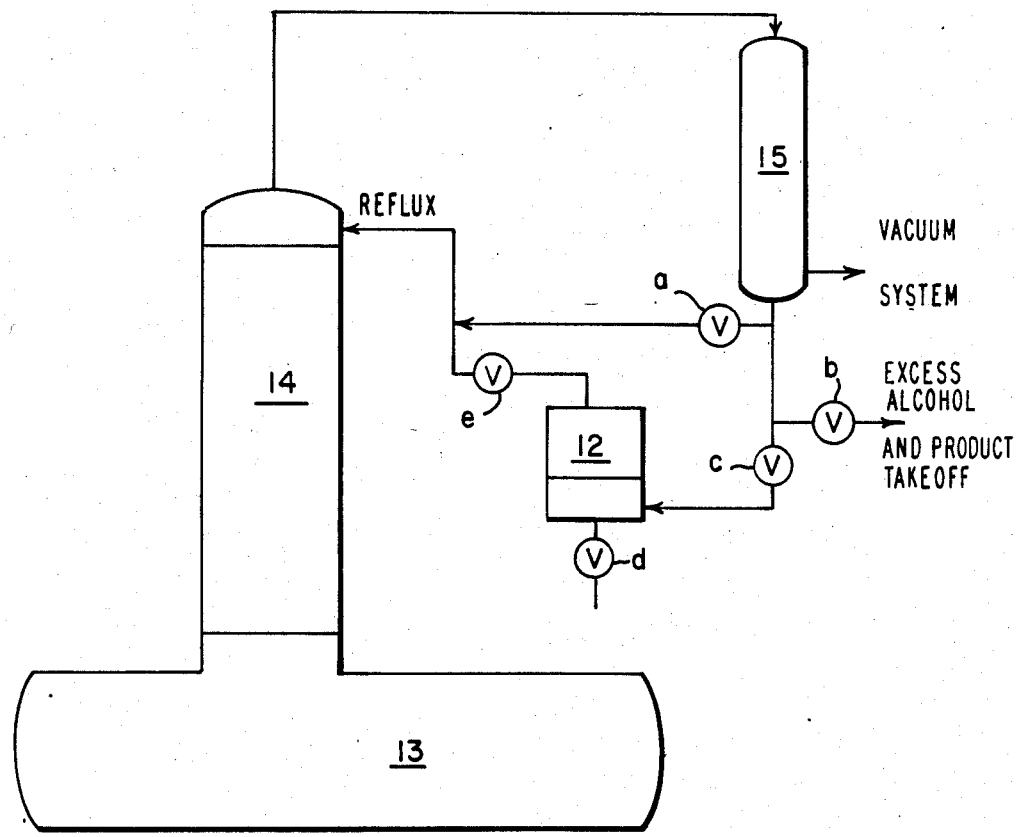

In the process of this invention methacrylic acid and n-butanol are added to a reaction vessel equipped with a distillation column. The reaction is a batch reaction. The initial ratio of n-butanol to methacrylic acid will preferably be between 1.1 to 1.5 (molar ratio), for greatest efficiency, although this ratio is not critical to the operation of the process.

A strong acid catalyst, such as sulfuric acid, toluene sulfonic acid, dodecyl benzene sulfonic acid, or a mixture of toluene sulfonic acid and xylene sulfonic acid, is present in an amount between 0.5 and 6 percent (most preferably 2–3 percent) based on weight of reaction mixture. A polymerization inhibitor, such as hydroquinone or the methyl ether of hydroquinone, is also employed.

The mixture is then heated to between about 95°–120° C. (vessel liquid temperature) both to start the reaction and to initiate boiling of the vessel contents. Initial temperature and pressure are not critical so long as boiling commences. Preferably, atmospheric pressure can be used initially. Slightly higher or lower pressures can be employed also, e.g. 30 to 150 kPa.

As the reaction proceeds, the water of reaction boils off along with n-butanol. The desired product, n-butyl methacrylate remains in the pot. Pressure is reduced as the concentration of n-butyl methacrylate increases to control vessel temperature and resultant polymer formation. Generally, pressure is lowered to approximately 40 kPa to maintain vessel temperature at 115° C.

The gaseous azeotrope of n-butanol and water is drawn off the distillate column. A column of 10 or more equilibrium stages is adequate to form this azeotrope. The azeotrope is condensed, whereupon it separates in a water-rich portion of about 92% water by weight and 8% butanol, and an n-butanol-rich portion of about 80% by weight butanol and 20% water. The n-butanol rich portion is returned to the system by putting it, as reflux liquid, into the distillation column.

When the methacrylic acid content of the pot is below 100 ppm the excess alcohol is removed from the column, and then the n-butyl methacrylate is removed.

The n-butyl methacrylate so obtained can be used as a comonomer to make copolymers, generally, with methyl methacrylate. Such copolymers can be used in latex paints and the like.

EXAMPLE 1

With reference to FIG. 1, 100 grams methacrylic acid, 130 grams n-butanol, 5 grams of a catalyst that is 70 weight % toluene sulfonic acid and 30% xylene sulfonic acid, and 1 gram hydroquinone were added to the still pot 6 of the laboratory batch distillation apparatus 5, (a 15 tray Older Shaw column). Along with a small air bleed (not shown) to the pot, the hydroquinone served to control polymer formation. This reaction mix was heated to boiling at atmospheric pressure and boilup was established in the distillation column. At this time still pot temperature was 115° C., and the temperature of the vapor at the top 4 of the distillation column 5 was 91° C. Distillate from the top was condensed in condenser 1. The condensate formed two phases on cooling. The heavier, water-rich phase was decanted off to vessel 2 and the lighter n-butanol-rich phase was returned as reflux liquid to the top (4) of distillation column (5).

Water-rich layer collection rate was as follows: five milliliters (ml) in the initial 15 minutes of the collection period; 12.7 ml total in 30 minutes; 21.7 ml total in 60 minutes; 22.5 ml total in 90 minutes with only fine droplets, of minor volume contribution to the total, collected at later time. The vapor or boilup rate in the column was 0.3 g/hr-g of reaction mixture charged as calculated from water phase collection rate. Then with steady heating and boilup maintained, methacrylic acid concentration of the still pot contents measured by gas chromatography was 0.27 wt. percent at two hours following initiation of boiling. One hour later this concentration was reduced to 130 parts per million (ppm). Finally, one hour later or four hours following initiation of boiling this methacrylic acid pot concentration was 23 ppm. During this entire reaction stage the still pot temperature was maintained at 115° C. by continual lowering of system pressure to compensate for the compositional change of the reaction mixture. Pressure was 460 mm Hg lower than atmospheric for the final stage of the reaction. Temperature of the overhead vapor at top 4 was 89° C. Unreacted butanol content of the pot was 10 wt. percent, or by computation a 20 percent excess butanol condition existed in the reaction mix.

At this time the reflux control 4 was adjusted to allow one part of the distillate condensate to be collected in receiver 3 for each one part of condensate returned to the distillation column. Unreacted, excess n-butanol was removed in this manner. In turn the n-butyl methacrylate product was collected in a separate receiver 3a that was connected at the same position. System pressure was continually lowered during this refining operation to minimize pot temperature and thus minimize n-butyl methacrylate polymer formation. Final pot temperature was 102° C. at a pressure 660 mm Hg below atmospheric pressure. Methacrylic acid content of the refined n-butyl methacrylate was 15 ppm as measured by alcoholic titration.

EXAMPLE 2

In similar manner to Example 1, 100 grams methacrylic acid, 145 grams n-butanol, 5 grams of the same catalyst used in Example 1 and 1 gram hydroquinone were added to the still pot of the apparatus in Example 1. With the only difference being a larger n-butanol charge, a steady boilup condition was established at atmospheric pressure and the pot temperature was maintained at 115° C. as the reaction progressed by appropriate pressure reduction. Distillate condensate again was two-phase, and the water-rich layer was easily separated from the butanol recycle. The methacrylic acid content of the reaction mixture was 1700 and 110 ppm at 2 and 3 hours, respectively, following initiation of boiling. Methacrylic acid content of refined n-butyl methacrylate recovered after 4 hours reaction time was 15 ppm. Excess butanol content of the reaction mix was 40 percent for this experiment.

EXAMPLE 3

In like manner to Examples 1 and 2, 100 grams methacrylic acid, 120 grams n-butanol, 5 grams of the same acid catalyst and 1 gram hydroquinone were added to the still pot. The lower butanol charge resulted in a 12 percent excess butanol reaction condition. Distillate condensate was two-phase and easily separable. In this case methacrylic acid content of the reaction mix was 2900 and 240 ppm at 2 and 3 hours reaction time. Methacrylic acid content of recovered n-butyl methacrylate product after 4 hours reaction time was 23 ppm.

EXAMPLE 4

Using the apparatus of Example 1, the pot charge was 100 grams methacrylic acid, 130 grams n-butanol, 50 grams n-butyl methacrylate, 6 grams of the same acid catalyst and 1 gram hydroquinone. The addition of n-butyl methacrylate simulated commercial batch operation for which a "heel" of product and catalyst would remain in the pot from batch to batch. This experiment also was begun at 400 mm Hg below atmospheric pressure. In turn, the initial boiling temperature of the reaction mix was only 102° C. The normal 115° C. reaction temperature was reached in 45 minutes, and pressure then was adjusted to maintain this value. Conversion rate was affected but slightly. Methacrylic acid content of the reaction mix at 2, 3 and 4 hours was 1800, 180 and 120 ppm, respectively, and 30 ppm for refined n-butyl methacrylate for the 4 hour reaction time.

However, coincident with the lower initial pressure, initial water content of the reaction mix was low at 0.2 wt. percent at 1 hour reaction time and in turn the corrosion rate of a 316 stainless steel coupon was less than 0.1 ml/year.

EXAMPLE 5

With reference to FIG. 2, 16,000 pounds methacrylic acid, 25,000 pounds n-butanol, 1,200 pounds of the same acid catalyst as used in Example 1 and 330 pounds of hydroquinone were charged to a still pot 13 equipped with distillation column 14. In addition, a decanter tank 12 was filled with n-butanol. With valves a, b and d closed, steam flow to a steam coil was initiated to establish a boiling condition in the still pot and buildup in the distillation column. Initial pressure at the top of the column was maintained at 350 mm Hg below atmospheric pressure. A steady boilup rate of 7000 pounds/hour was established and the initial pot temperature was 95° C. This pot temperature slowly increased to about 113° C. during the reaction step, and pressure was maintained constant during this time. Methacrylic acid content of the reaction mixture was 3 wt. percent 2 hours after steady boilup was established, 3000 ppm at 3 hours, 400 ppm at 4 hours, 100 ppm at 5 hours and 60 ppm at 5.5 hours.

The butanol/water azeotrope was collected in the decant tank 12 where it separated. The n-butanol rich layer was then added to column 14 through valve e. The liquid-liquid interface in the decant tank was not monitored during the operation. The presence of the water was verified at the end of the experiment by draining through valve d. Alcohol and ester were removed via valve b.

EXAMPLE 6

Using the equipment shown in FIG. 2, 19,000 pounds methacrylic acid, 20,000 pounds n-butanol were added to the still pot which contained 5500 pounds of "heel" remaining from the previous batch. This heel was made up of approximately 1200 pounds the same acid catalyst used in Example 5, less than 1000 pounds hydroquinone, less than 500 pounds polymer, with the remainder being n-butyl methacrylate. Analogous to Example 5, steady boilup was established with valves a, b and d closed. However, in this case boilup rate was only 3000 pounds/hour initially and increased to 6000 pounds/hour at the end of the reaction step. Methacrylic acid content of the reaction mixture decreased with time following initiation of boilup as follows, 16 weight percent at 2 hours, 3 weight percent at 4 hours, 3700 ppm at 6 hours, 130 ppm at 8 hours and 45 ppm at 10 hours.

The still pot contained a total of 34,000 pounds of n-butyl methacrylate product at this time. (In contrast only 26,000 pounds of product would have been made in the same equipment by transesterification of methyl methacrylate. In transesterification, the methanol of reaction cannot be decanted off as a second phase, and significant methyl methacrylate reactant is removed as an azeotropic mixture with the methanol. Thus, yield to product is reduced).

At this time valves c and e were closed and valves a and b were opened. Flow was split between reflux to the column and takeoff in the ratio 2/1, and pressure at the top of the column was lowered to 50 mm Hg absolute.

Thirteen thousand pounds of distillate were collected which contained on average 47 weight percent n-butanol and 53 weight percent n-butyl methacrylate. Reflux to takeoff ratio then was changed to 1/10 and refined n-butyl methacrylate was diverted to a separate tank. Twenty four thousand five hundred pounds were isolated as refined product with a methacrylic acid content of 86 ppm.

We claim:

1. A batch process for making n-butyl methacrylate which comprises reacting methacrylic acid and n-butanol in a reaction vessel equipped with a distillation column, said vessel containing a strong acid catalyst present in an amount of between 0.5 to 6 percent by weight based on total weight of reaction mixture, the initial mole ratio of n-butanol to methacrylic acid being between 1.1 to 1.5, the temperature in the reaction vessel being maintained between 95° and 120° C. and the pressure being between 30 and 150 kPa, while
    a. collecting gaseous n-butanol-water azeotrope distillate from the distillation still,
    b. condensing the azeotrope distillate substantially free from n-butyl methacrylate collected from step a.,
    c. separating the water-rich layer from the n-butanol-rich layer of the distillate condensed in step b, and
    d. returning the n-butanol-rich layer as reflux liquid to the distillation column, said process being carried out until the methacrylic acid is substantially used up, whereupon n-butyl methacrylate is recovered from the reaction vessel.

* * * * *